US010090611B2

(12) United States Patent
Sekido

(10) Patent No.: US 10,090,611 B2
(45) Date of Patent: Oct. 2, 2018

(54) CABLE, CABLE CONNECTION STRUCTURE, AND IMAGING APPARATUS

(71) Applicant: OLYMPUS CORPORATION, Tokyo (JP)

(72) Inventor: Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 875 days.

(21) Appl. No.: 14/331,618

(22) Filed: Jul. 15, 2014

(65) Prior Publication Data

US 2014/0326857 A1 Nov. 6, 2014

Related U.S. Application Data

(63) Continuation of application No. PCT/JP2013/050840, filed on Jan. 17, 2013.

(30) Foreign Application Priority Data

Jan. 18, 2012 (JP) .................................. 2012-008371

(51) Int. Cl.
| | | |
|---|---|---|
| *A61B 1/04* | (2006.01) | |
| *H01R 12/71* | (2011.01) | |
| *H01R 12/53* | (2011.01) | |
| *H01B 7/17* | (2006.01) | |
| *H01L 27/146* | (2006.01) | |
| *A61B 1/00* | (2006.01) | |
| *A61B 1/05* | (2006.01) | |

(52) U.S. Cl.
CPC ........ *H01R 12/718* (2013.01); *A61B 1/00114* (2013.01); *A61B 1/05* (2013.01); *H01B 7/17* (2013.01); *H01L 27/14636* (2013.01); *H01R 12/53* (2013.01)

(58) Field of Classification Search
None
See application file for complete search history.

(56) References Cited

U.S. PATENT DOCUMENTS 5,879,285 A * 3/1999 Ishii .......................... A61B 1/05
348/75
2013/0064530 A1 3/2013 Sekido

FOREIGN PATENT DOCUMENTS

| JP | 57-138288 | 8/1982 |
|---|---|---|
| JP | 5-159815 A | 6/1993 |
| JP | 2000-82834 A | 3/2000 |
| JP | 2006-100204 A | 4/2006 |

(Continued)

OTHER PUBLICATIONS

International Search Report dated Feb. 26, 2013 from related International Application No. PCT/JP2013/050840.

(Continued)

*Primary Examiner* — James Anderson, II
(74) *Attorney, Agent, or Firm* — Scully, Scott, Murphy & Presser, P.C.

(57) ABSTRACT

A cable includes: a core wire that is electrically conductive; a first inner insulation layer that covers an outer periphery of the core wire and has an exposing portion that exposes the core wire at a distal end side of the first inner insulation layer; and a first latching portion that is fixed to the core wire in the exposing portion, and is latched onto the first inner insulation layer and holds the core wire by coming into contact with the first inner insulation layer.

4 Claims, 13 Drawing Sheets

(56) References Cited

FOREIGN PATENT DOCUMENTS

| | | | |
|---|---|---|---|
| JP | 3863583 B2 | | 10/2006 |
| JP | 2010-56033 A | | 3/2010 |
| JP | 2010056033 A | * | 3/2010 |
| JP | 2011-34766 A | | 2/2011 |
| JP | 2011034766 A | * | 2/2011 |
| JP | 2011-238458 A | | 11/2011 |
| WO | 2011/142322 A1 | | 11/2011 |

OTHER PUBLICATIONS

English language abstract of JP 09-090237 dated Apr. 4, 1997 (corresponds to JP 3863583).

* cited by examiner

CABLE, CABLE CONNECTION STRUCTURE, AND IMAGING APPARATUS

CROSS REFERENCES TO RELATED APPLICATIONS

This application is a continuation of PCT international application Ser. No. PCT/JP2013/050840 filed on Jan. 17, 2013 which designates the United States, incorporated herein by reference, and which claims the benefit of priority from Japanese Patent Application No. 2012-008371, filed on Jan. 18, 2012, incorporated herein by reference.

BACKGROUND

1. Technical Field

The disclosure relates to a cable, a cable connection structure that connects the cable to a substrate, and an imaging apparatus using the cable connection structure.

2. Related Art

In recent years, medical and industrial endoscopes have been used widely. An example of a medical endoscope is an imaging apparatus that has a built-in imaging element, such as a CCD, at a distal end of an insertion portion to be inserted into a body. By inserting the insertion portion deeply into the body, a lesion part can be observed, and also, by using a treatment tool therewith as necessary, examination and treatment inside the body can be performed.

In such an endoscope, in order to project an image onto a monitor, image information captured by an imaging element is converted into an electric signal, the electric signal is transmitted to a signal processing apparatus via a signal line, and the transmitted signal is processed in this signal processing apparatus. The imaging element in the endoscope is connected to the signal processing apparatus by a cable assembly bundled of a plurality of cables for transmission of image signals, transmission of clock signals, supply of drive power to the imaging element, and the like.

As a technique related to connection of the cable assembly, in Japanese Patent No. 3863583, a technique of collectively connecting a cable assembly formed of a plurality of coaxial cables to a circuit board, on which an electrode is provided, is disclosed. In this technique, first, a distal end portion of each coaxial cable is fixed by an array block, and a polishing process is performed such that a distal end surface of an electric wire of each coaxial cable matches with a distal end surface of the array block. Thereafter, these distal end surfaces of the electric wires are placed opposite to the circuit board on which the electrode is provided and they are connected to each other via an anisotropic conductive sheet, a connection bump, and the like. Further, for reinforcement, an epoxy-based adhesive is applied around this connected part and hardened.

SUMMARY

In accordance with some embodiments, a cable, a cable connection structure that connects the cable to a substrate, and an imaging apparatus using the cable connection structure are presented.

In some embodiments, a cable includes: a core wire that is electrically conductive; a first inner insulation layer that covers an outer periphery of the core wire and has an exposing portion that exposes the core wire at a distal end side of the first inner insulation layer; and a first latching portion that is fixed to the core wire in the exposing portion, and is latched onto the first inner insulation layer and holds the core wire by coming into contact with the first inner insulation layer.

In some embodiments, a cable connection structure includes: a cable that has at least a core wire that is electrically conductive and a first inner insulation layer that covers an outer periphery of the core wire and has an exposing portion that exposes the core wire at a distal end side of the first inner insulation layer; a first latching portion that is fixed to the core wire in the exposing portion, and is latched onto the first inner insulation layer and holds the core wire by coming into contact with the first inner insulation layer; and a circuit board that has an electrode electrically connected to the core wire.

In some embodiments, an imaging apparatus includes: the above-described cable connection structure; and an imaging element that is connected to an external electrode formed on the circuit board of the cable connection structure and converts light incident from outside into an electric signal.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the present invention will be described in detail with the drawings. The present invention is not limited by the following embodiments. Further, each drawing referred to in the following description schematically illustrates shapes, sizes, and positional relations merely to an extent that allows contents of the present invention to be understood. That is, the present invention is not limited only to the shapes, sizes, and positional relations exemplified in each drawing. In the following description, an endoscope apparatus will be described as an example of an imaging apparatus.

First Embodiment

Figure 1:
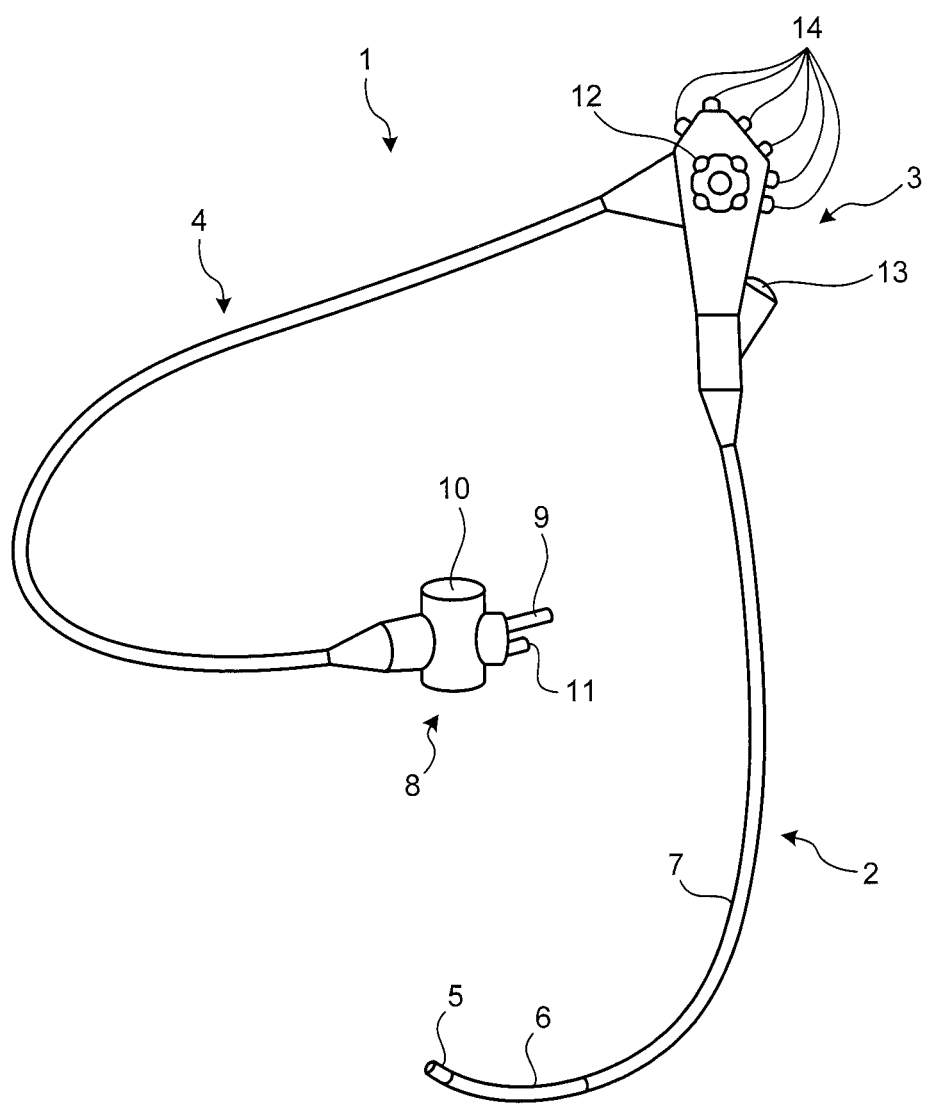
FIG. 1 is a schematic diagram illustrating an overall configuration of an endoscope apparatus according to a first embodiment of the present invention.

First, an endoscope apparatus of a first embodiment will be described. FIG. 1 is a diagram illustrating a schematic configuration of an endoscope apparatus 1 having a cable connection structure 100 according to this first embodiment. As illustrated in FIG. 1, an endoscope apparatus 1 according to this embodiment includes: an insertion portion 2 that is elongated; an operating unit 3 that is at a proximal end side of this insertion portion 2 and held by an endoscope apparatus operator; and a universal cord 4 that extends from a side portion of this operating unit 3 and is flexible. The universal cord 4 has a light guide cable, an electrical cable, and the like, built-in therein.

The insertion portion 2 includes: a distal end portion 5 that has therein an imaging element, such as a CCD; a bending portion 6 that is formed of a plurality of bending pieces and is freely bendable; and a flexible tube portion 7 that is provided at a proximal end side of this bending portion 6, is long, and has flexibility.

At an extending side end portion of the universal cord 4, a connector unit 8 is provided; and in this connector unit 8, a light guide connector 9 that is detachably connected to a light source device, an electric contact unit 10 for transmitting an electric signal of a subject image photoelectrically converted by the CCD or the like to a signal processing apparatus or a control device, an air supply mouthpiece 11 for sending air to a nozzle of the distal end portion 5, and the like are provided. The light source device has a halogen lamp or the like therein and supplies light from the halogen lamp as illumination light to the endoscope apparatus 1 connected via the light guide connector 9. Further, the signal processing apparatus and the control device are an apparatus and a device, which supply electric power to the imaging element and into which an electric signal photoelectrically converted is input from the imaging element, and the signal processing apparatus and the control device process the electric signal captured by the imaging element, cause the connected display device to display an image, and perform control such as gain adjustment of the imaging element and outputting of a drive signal to perform driving of the imaging element.

The operating unit 3 is provided with a bending knob 12 that bends the bending portion 6 in a vertical direction and a horizontal direction; a treatment tool insertion portion 13 through which a treatment tool such as biopsy forceps, a laser probe, or the like are/is inserted into a body cavity; and a plurality of switches 14 that perform operations of peripheral devices such as the signal processing apparatus and the control device, or air supply, water supply, and gas supply means. The endoscope apparatus 1, in which the treatment tool has been inserted in a treatment unit insertion opening causes a distal end treatment unit of the treatment tool to protrude via a treatment tool insertion channel provided inside thereof and performs a biopsy or the like of collecting affected tissue by the biopsy forceps, for example.

Figure 2:
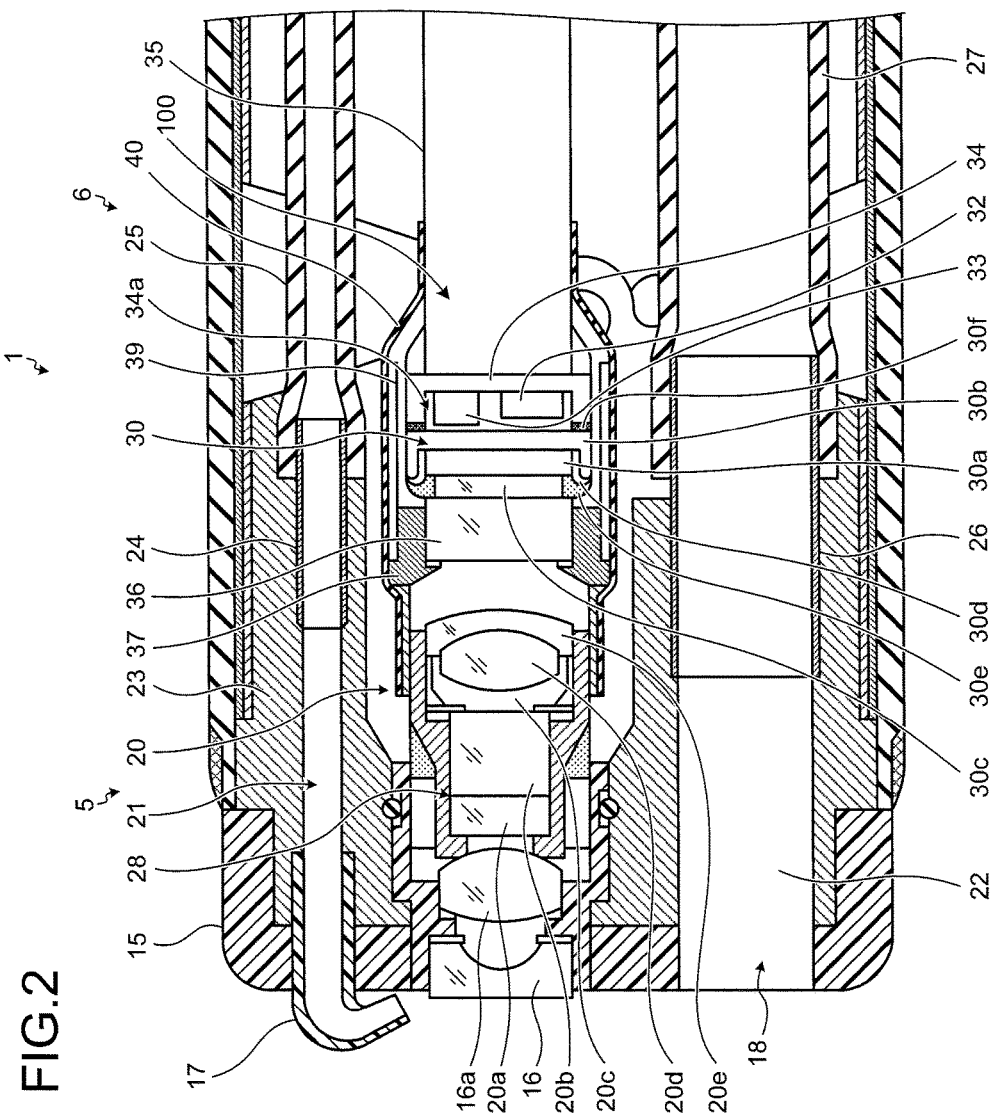
FIG. 2 is a cross section diagram illustrating an internal configuration of a distal end portion of the endoscope apparatus illustrated in FIG. 1.

Next, a configuration of the distal end portion of the endoscope apparatus 1 will be described. FIG. 2 is a cross section diagram illustrating an internal configuration of the distal end portion 5 of the endoscope apparatus 1 illustrated in FIG. 1. As illustrated in FIG. 2, the distal end portion 5 positioned at a distal end side of the insertion portion 2 of the endoscope apparatus 1 has a distal end portion that is externally fitted with a distal end cover 15. In the distal end cover 15, an observation window 16, an illumination lens not illustrated, a nozzle 17 for supplying air and supplying water, and a forceps opening 18 are provided. In the observation window 16, an imaging device 20 that captures an image inside the body cavity is inserted, via a plurality of lenses including a lens 16a. Further, behind the observation window 16, a distal end block 23 is arranged, in which an air supply and water supply hole 21, a forceps insertion hole 22, and the like are provided to respectively correspond to the nozzle 17 and the forceps opening 18.

At a rear end portion of the air supply and water supply hole 21 in the distal end block 23, an air supply and water supply pipe 24 is provided, and to this air supply and water supply pipe 24, an air supply and water supply tube 25 is connected. At a rear end portion of the forceps insertion hole 22, a forceps insertion pipe 26 is provided, and to this forceps insertion pipe 26, a forceps insertion tube 27 is connected.

The imaging device 20 includes: an objective optical unit 28 formed of a plurality of optical lenses 20a to 20e; a CCD 30 that is arranged behind this objective optical unit 28 and receives light incident on the objective optical unit 28; and the cable connection structure 100 that transmits an image signal in this CCD 30 to the signal processing apparatus, which is an external device.

At a light receiving surface side of the CCD 30, a cover glass 36 is provided, and to an outer peripheral portion of this cover glass 36, an inner peripheral portion of a CCD holding frame 37 is fitted and integrally fixed thereto by an adhesive or the like. The CCD 30 includes: a CCD chip 30a having an imaging unit; a package 30b; a filter 30c; a bonding wire 30d; a sealing resin 30e; an electrode 30f; and the like, for example.

The cable connection structure 100 includes: a circuit board 34 on which an IC 32 that processes the image signal received from the CCD 30 into an electric signal and a chip condenser 33 are mounted; and a coaxial cable 35 (cable) that transmits the electric signal to the signal processing apparatus, which is the external device.

The circuit board 34 has electrode portions provided on both sides thereof. On an imaging device 20 side of the circuit board 34, a concave portion 34a, in which the IC 32 and the chip condenser 33 are mounted, is provided. The electrode provided at the imaging device 20 side of the circuit board 34 is connected to the electrode 30f of the CCD 30.

At a rear end portion of the CCD holding frame 37, a shield frame 39 is provided to cover the CCD 30 and the circuit board 34. This shield frame 39, and an outer peripheral portion distal end side of the CCD holding frame 37 are covered by a thermal shrinking tube 40. The CCD 30 is from a distal end portion of the CCD holding frame 37 up to a rear end of the coaxial cable 35, and a hard portion of the imaging device 20 is from a distal end surface of the CCD holding frame 37 up to a rear end of the thermal shrinking tube 40.

Figure 3:
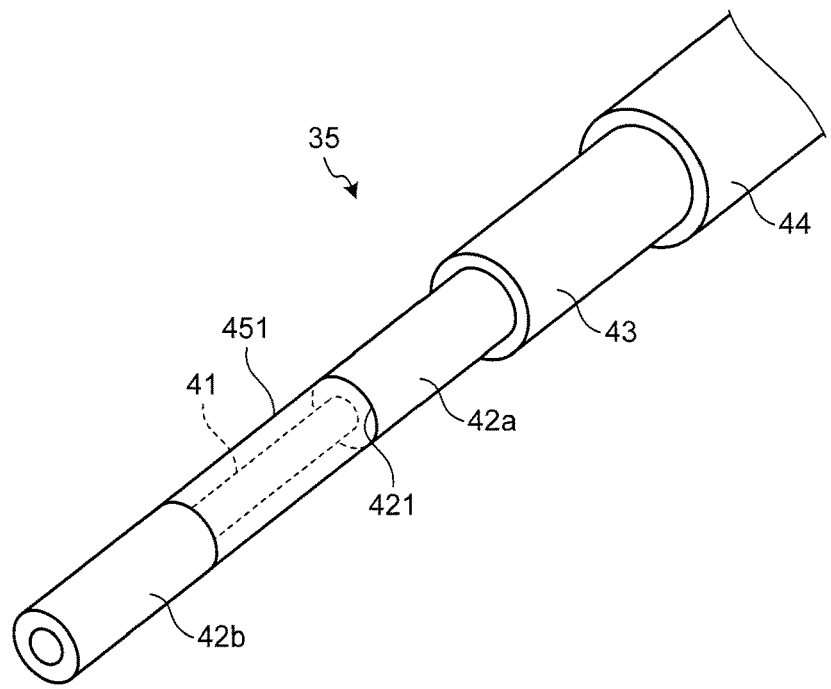
FIG. 3 is a perspective diagram illustrating a cable of a cable connection structure according to the first embodiment of the present invention.
Figure 4:
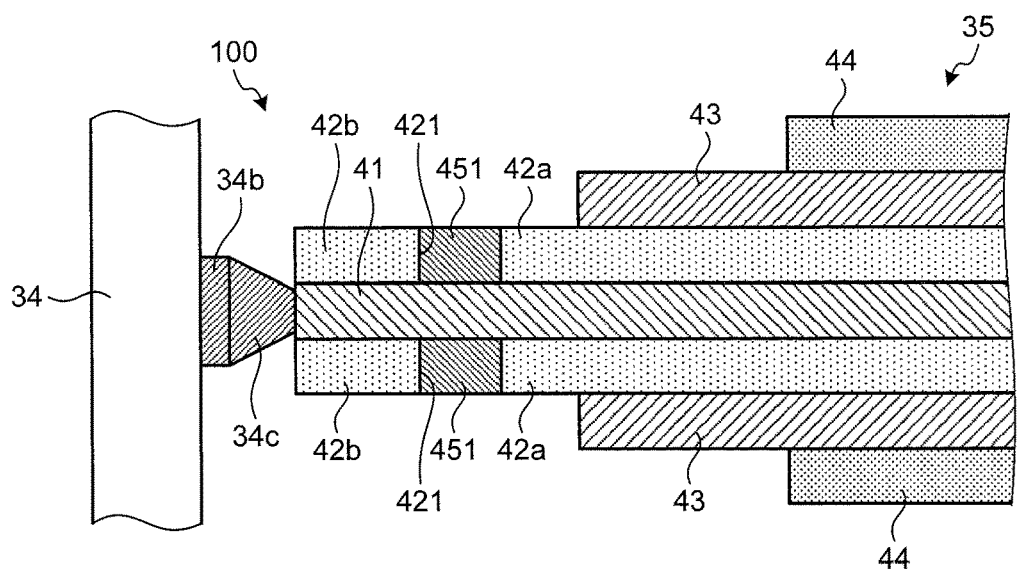
FIG. 4 is a cross section diagram illustrating the cable connection structure according to the first embodiment of the present invention.

Next, the cable connection structure 100 according to the first embodiment will be described. FIG. 3 is a perspective diagram illustrating the coaxial cable 35 of the cable connection structure 100 according to the first embodiment. FIG. 4 is a cross section diagram illustrating a cable connection structure 100 according to the first embodiment.

The coaxial cable 35 includes: a core wire 41 formed of a conductive body made of copper or the like; a first inner insulation layer 42a that is formed of an insulator, covers an outer periphery of the core wire 41, and has an exposing portion 421 at a distal end side thereof that exposes the core wire 41; a second inner insulation layer 42b that is provided at a distal end of the core wire 41 and covers a part of the exposing portion 421; a shield wire 43 that covers an outer periphery of the first inner insulation layer 42a and is formed of a conductive body; and an outer insulation layer 44 that covers an outer periphery of the shield wire 43 and is formed of an insulator. In the coaxial cable 35, at an end portion at a side connected to the circuit board 34, the first inner insulation layer 42a, the shield wire 43, and the outer insulation layer 44 are formed by being subjected to a step-stripping process.

On the circuit board 34, an electrode 34b is formed on a side connected to the coaxial cable 35. The core wire 41 and the electrode 34b are fixed by a connection bump 34c and electrically connected to each other. The connection bump 34c is formed of an electrically conductive material such as a solder, gold (Au), or the like.

The coaxial cable 35 includes, at the exposing portion 421 between the first inner insulation layer 42a and the second inner insulation layer 42b, a latching portion 451 (first latching portion) which is fixed to the core wire 41, fitted into the exposing portion 421, and is latched onto the first inner insulation layer 42a and holds the core wire 41. The latching portion 451 is formed by being filled into an internal space formed by the first inner insulation layer 42a and the second inner insulation layer 42b (exposing portion 421), by a plating process. When that is done, a diameter of the latching portion 451 in a direction orthogonal to a direction, in which the coaxial cable 35 extends, is preferably equal to or less than a diameter of the first inner insulation layer 42a in the direction orthogonal to the direction, in which the coaxial cable 35 extends. Further, the latching portion 451 is formed of an electrically conductive material, such as nickel. The latching portion 451 may be made: by application of an electrically conductive paste; or by being fixed to the core wire 41 by an adhesive, other than by the plating process. Further, the latching portion 451 may be a non-electrically-conductive material, such as an epoxy resin.

In the coaxial cable 35, even if a load in a pulling direction acts on the core wire due to deformation of the cable, stripping at the other end after cable connection, or the like, the latching portion 451 coupled to the core wire 41 is in contact with an end face of the first inner insulation layer 42a and thus the core wire 41 will not be shifted from the first inner insulation layer 42a. Thereby, even if the load in the pulling direction acts on the core wire due to the deformation of the cable, the stripping at the other end after the cable connection, or the like, connection between an end face of the core wire 41 and the connection bump can be prevented from being destroyed.

According to the above described first embodiment, by the coaxial cable 35 having the latching portion 451, which is fixed to the core wire 41, latched onto the first inner insulation layer 42a, even if the load in the pulling direction acts on the core wire 41 by the deformation of the cable, the stripping at the other end after the cable connection, or the like, the connection between the end face of the core wire 41 and the connection bumps is able to prevented from being destroyed and reliability of connection between a cable and a circuit board can be improved.

Figure 5:
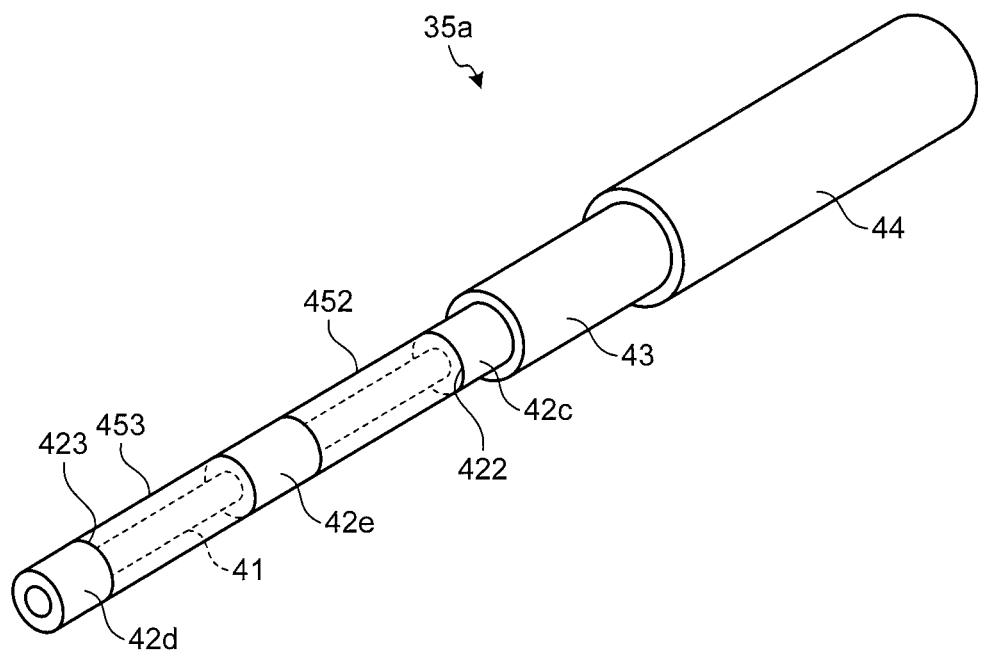
FIG. 5 is a perspective diagram illustrating a cable of a cable connection structure according to a modified example 1-1 of the first embodiment of the present invention.
Figure 6:
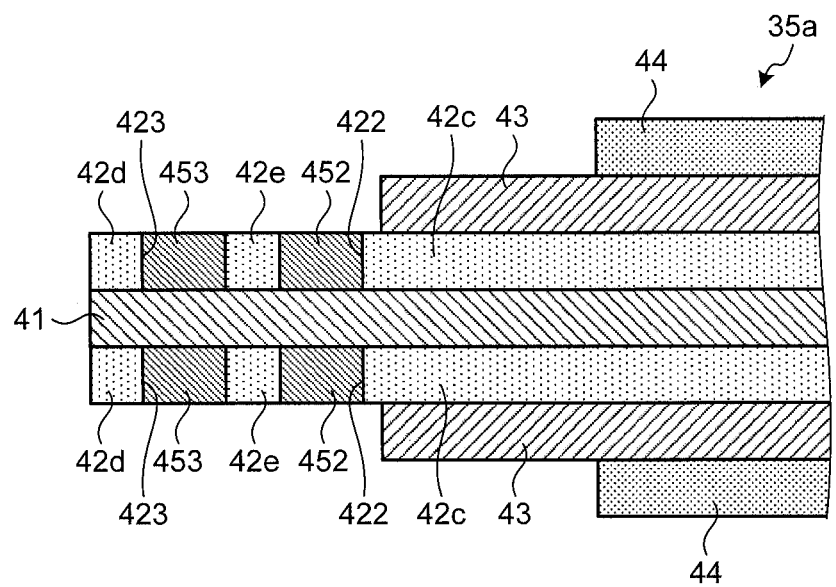
FIG. 6 is a cross section diagram illustrating the cable of the cable connection structure according to the modified example 1-1 of the first embodiment of the present invention.

FIG. 5 is a perspective diagram illustrating a coaxial cable 35a of a cable connection structure according to a modified example 1-1 of the first embodiment. FIG. 6 is a cross section diagram illustrating the coaxial cable 35a of the cable connection structure according to the modified example 1-1 of the first embodiment. The above described first embodiment has been described as having one space in which the latching portion is provided, but a plurality of the latching portions may be provided like in the modified example 1-1.

The coaxial cable 35a illustrated in FIGS. 5 and 6 includes a third inner insulation layer 42e, which is provided between a first inner insulation layer 42c and a second inner insulation layer 42d and covers a part of an exposing portion. Thereby, exposing portions 422 and 423 are respectively formed between the first inner insulation layer 42c and the third inner insulation layer 42e, and between the second inner insulation layer 42d and the third inner insulation layer 42e. Further, the coaxial cable 35a has latching portions 452 and 453 (first latching portion), which are fixed to the core wire 41, are respectively fitted into the exposing portions 422 and 423, and are latched onto the first inner insulation layer 42c and the third inner insulation layer 42e and hold the core wire 41. The latching portions 452 and 453 are formed by respectively being filled, by a plating process, into internal spaces formed by the exposing portions 422 and 423, similarly to the latching portion 451. Further, the latching portions 452 and 453 are formed of an electrically conductive material, such as nickel (Ni).

According to the above described modified example 1-1, by providing the plural latching portion 452 and 453, an area to receive a force in a pulling direction of the core wire 41 can be increased, and connection strength against a load in the pulling direction placed on the core wire 41 can be increased.

Figure 7:
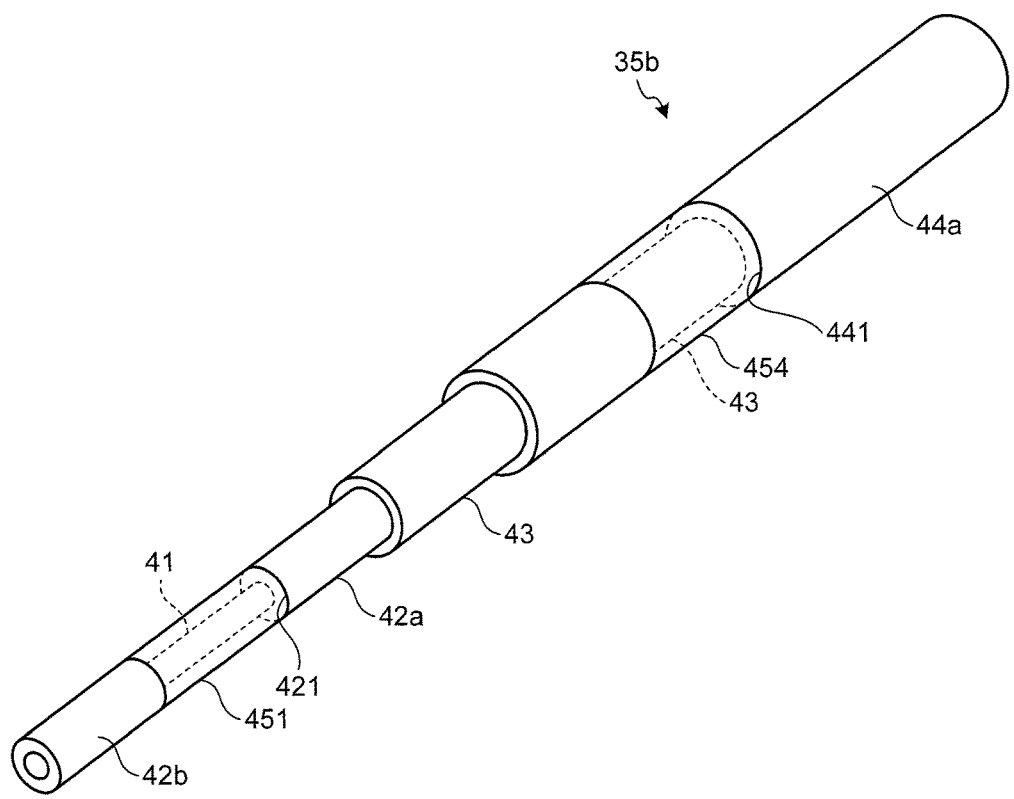
FIG. 7 is a perspective diagram illustrating a cable of a cable connection structure according to a modified example 1-2 of the first embodiment of the present invention.
Figure 8:
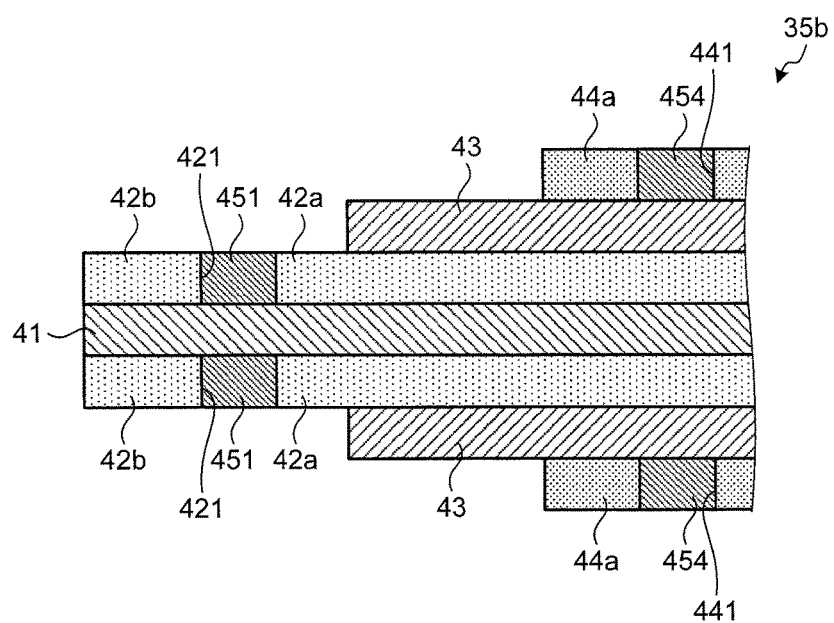
FIG. 8 is a cross section diagram illustrating the cable of the cable connection structure according to the modified example 1-2 of the first embodiment of the present invention.

FIG. 7 is a perspective diagram illustrating a coaxial cable 35b of a cable connection structure according to a modified example 1-2 of the first embodiment. FIG. 8 is a cross section diagram illustrating the coaxial cable 35b of the cable connection structure according to the modified Example 1-2 of the first embodiment. According to the description of the above described first embodiment, the exposing portion is provided in the first inner insulation layer, but like in the modified example 1-2, a hollowed portion, which has a configuration comparable to the exposing portion, may be provided in an outer insulation layer.

The coaxial cable 35b illustrated in FIGS. 7 and 8 has the above described exposing portion 421 and a hollowed portion 441 formed therein, the hollowed portion 441 being provided in an outer insulation layer 44a and hollowed so as to expose an outer periphery of the shield wire 43. Further, the coaxial cable 35b has the above described latching portion 451 and a latching portion 454 (second latching portion) which is fixed to the shield wire 43, is fitted into the hollowed portion 441, and is latched onto the outer insulation layer 44a and holds the shield wire 43. The latching portion 454 is formed, similarly to the latching portion 451, by being filled, by a plating process, into an inner space formed by the hollowed portion 441. Further, the latching portion 454 is formed of an electrically conductive material, such as nickel (Ni).

According to the above described modified example 1-2, in addition to preventing the shifting of the core wire 41 by the latching portion 451, even if a load in a pulling direction acts on the core wire due to deformation of the core wire 41, stripping at the other end after cable connection, or the like, since the latching portion 454 coupled to the shield wire 43 is in contact with a wall surface of the hollowed portion 441 of the outer insulation layer 44a, the shield wire 43 is prevented from shifting from the outer insulation layer 44a. Thereby, even if the load in the pulling direction acts on the core wire due to the deformation of the cable, the stripping at the other end after the cable connection, or the like, connection between end faces of the core wire 41 and shield wire 43 and the connection bump can be prevented from being destroyed, and a stable connection state can be maintained by preventing the shift between the shield wire 43 and the outer insulation layer 44a.

Figure 9:
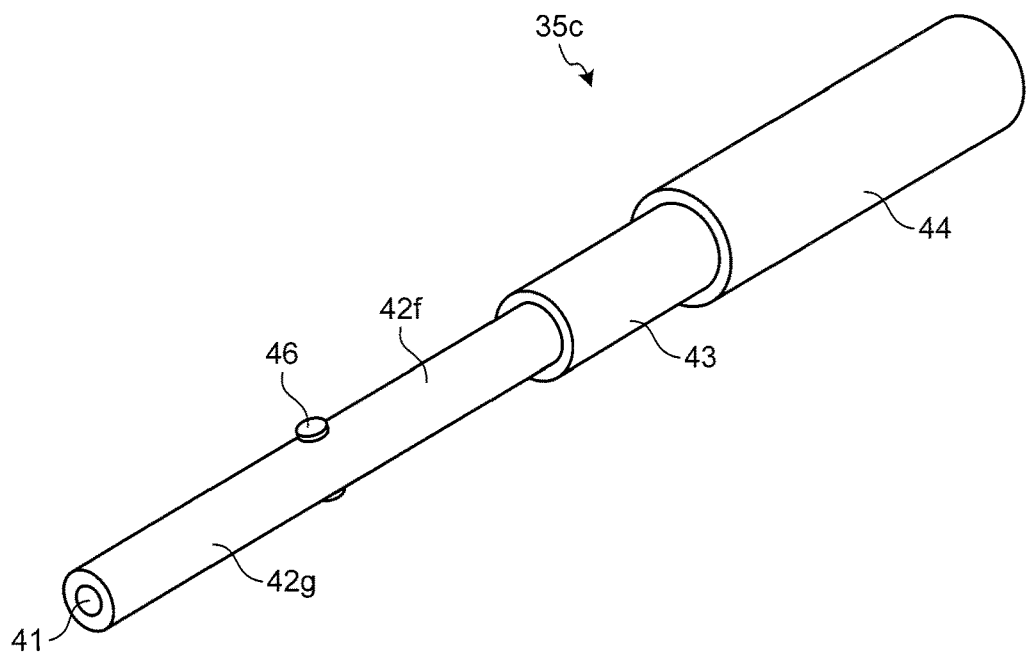
FIG. 9 is a perspective diagram illustrating a cable of a cable connection structure according to a modified example 1-3 of the first embodiment of the present invention.
Figure 10:
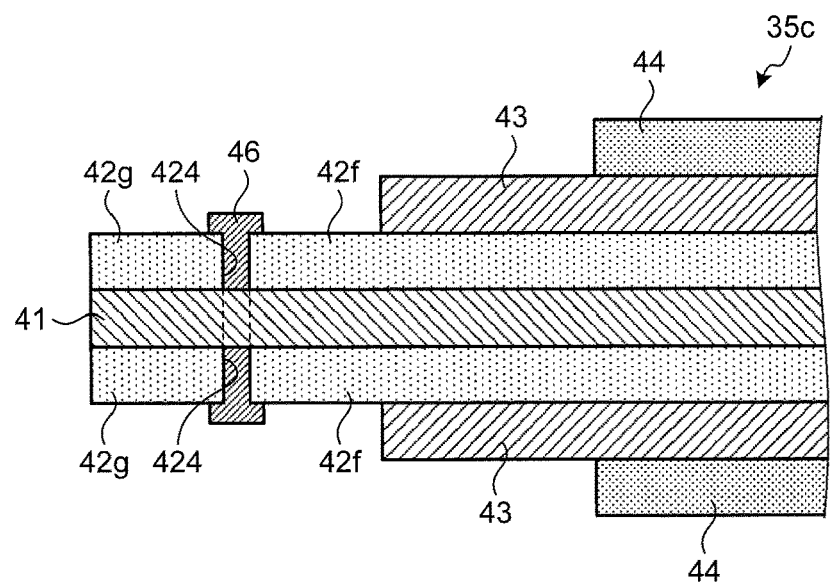
FIG. 10 is a cross section diagram illustrating the cable of the cable connection structure according to the modified example 1-3 of the first embodiment of the present invention.

FIG. 9 is a perspective diagram illustrating a coaxial cable 35c of a cable connection structure according to a modified example 1-3 of the first embodiment. FIG. 10 is a cross section diagram illustrating the coaxial cable 35c of the cable connection structure according to the modified example 1-3 of the first embodiment. According to the above description of the first embodiment, the exposing portion and the latching portion are provided over a whole circumference of the cable side surface, but like in the modified example 1-3, an exposing portion and a latching portion may be provided partially on a peripheral surface.

The coaxial cable 35c illustrated in FIGS. 9 and 10 includes: a first inner insulation layer 42f that covers an outer periphery of the core wire 41; and a second inner insulation layer 42g that extends from an end portion of the first inner insulation layer 42f at a distal end side of the coaxial cable 35c and covers an outer periphery of the core wire 41. The second inner insulation layer 42g has an exposing portion 424 formed in a direction orthogonal to the longitudinal direction, which is hollowed to intersect a central axis of the second inner insulation layer 42g in a longitudinal direction thereof. Further, the coaxial cable 35c has a pin 46 (first latching portion) that is inserted through the core wire 41 and exposing portion 424, is latched onto the first inner insulation layer 42f and holds the core wire 41 via a part of the second inner insulation layer 42g. A diameter of the pin 46 in a direction orthogonal to this insertion direction is less than a diameter of the core wire 41. If the core wire 41 is formed of a bundle of a plurality of conductive wires, the pin 46 is inserted through between the respective conductive wires. Further, if the core wire 41 is a single wire, a hole, through which the pin 46 is inserted, is preferably provided therein. The pin 46 is formed of an electrically conductive material, such as copper (Cu), or an insulating material, such as a resin.

Figure 11:
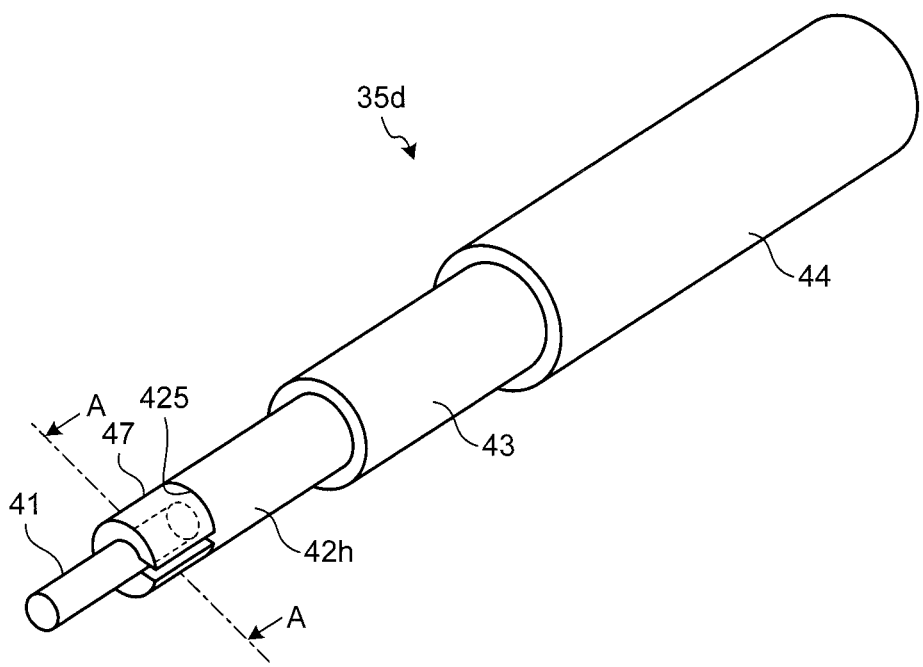
FIG. 11 is a perspective diagram illustrating a cable of a cable connection structure according to a modified example 1-4 of the first embodiment of the present invention.
Figure 12:
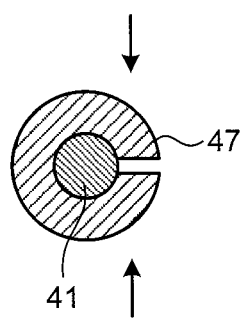
FIG. 12 is a cross section diagram illustrating an A-A line cross section illustrated in FIG. 11.

FIG. 11 is a perspective diagram illustrating a coaxial cable 35d of a cable connection structure according to a modified example 1-4 of the first embodiment. FIG. 12 is a cross section diagram illustrating an A-A line cross section illustrated in FIG. 11. According to the above description of the first embodiment, the latching portion corresponding to the exposing portion is provided, but like in the modified example 1-4, a latching member fixed to the core wire 41 may be brought into contact with an end face of a first inner insulation layer.

The coaxial cable 35d illustrated in FIGS. 11 and 12 has a latching member 47 (first latching portion), which covers an outer periphery of the core wire 41, is provided in contact with an end face of a first inner insulation layer 42h having at a distal end side thereof an exposing portion 425 to expose the core wire 41, is fixed to the core wire 41, and is latched onto the first inner insulation layer 42h and holds the core wire 41. The latching member 47 is approximately C-shaped, and when a load is added in a vertical direction of the C-shape, a diameter of a ring-shaped inner space formed by both ends thereof being in contact with each other is less than a diameter of the core wire 41 (see FIG. 12). Thereby, the latching member 47 caulks and fixes the core wire 41 in a state of being in contact with the end face of the first inner insulation layer 42h. The latching member 47 is formed of an electrically conductive material, such as cupper (Cu) or aluminum (Al), or an insulating material, such as a resin.

Figure 13:
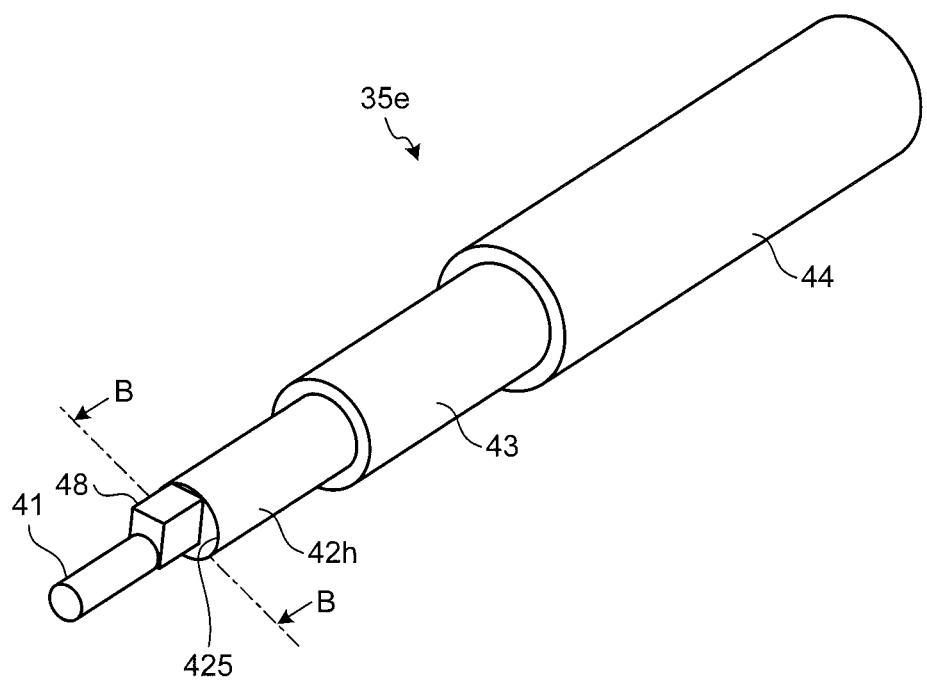
FIG. 13 is a perspective diagram illustrating a cable of a cable connection structure according to a modified example 1-5 of the first embodiment of the present invention.
Figure 14:
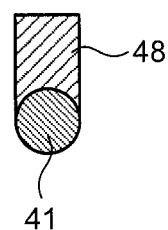
FIG. 14 is a cross section diagram illustrating a B-B line cross section illustrated in FIG. 13.

Further, FIG. 13 is a perspective diagram illustrating a coaxial cable 35e of a cable connection structure according to a modified example 1-5 of the first embodiment. FIG. 14 is a cross section diagram illustrating a B-B line cross section illustrated in FIG. 13. The coaxial cable 35e illustrated in FIGS. 13 and 14 has a latching member 48 (first latching portion), which is provided in contact with the end face of the first inner insulation layer 42h, is fixed to the core wire 41, and is latched onto the first inner insulation layer 42h and holds the core wire 41. The latching member 48 is approximately column shaped and fixed to the core wire 41. The latching member 48 is formed of an electrically conductive material, such as nickel (Ni), or an insulating material, such as a resin.

According to the above described modified examples 1-4 and 1-5, by fixing the latching member to the core wire 41 at the position that has been brought into contact with the end face of the first inner insulation layer 42h, even if a load in a pulling direction acts on the core wire 41 due to the deformation of the cable of the core wire 41, stripping at the other end after cable connection, or the like (in a drawn direction into the first inner insulation layer 42h), the core wire 41 is prevented from shifting from the first inner insulation layer 42h. Thereby, even if the load in the pulling direction acts on the core wire due to the deformation of the cable, the stripping at the other end after the cable connection, or the like, connection between an end face of the core wire 41 and a connection bump can be prevented from being destroyed.

Second Embodiment

Figure 15:
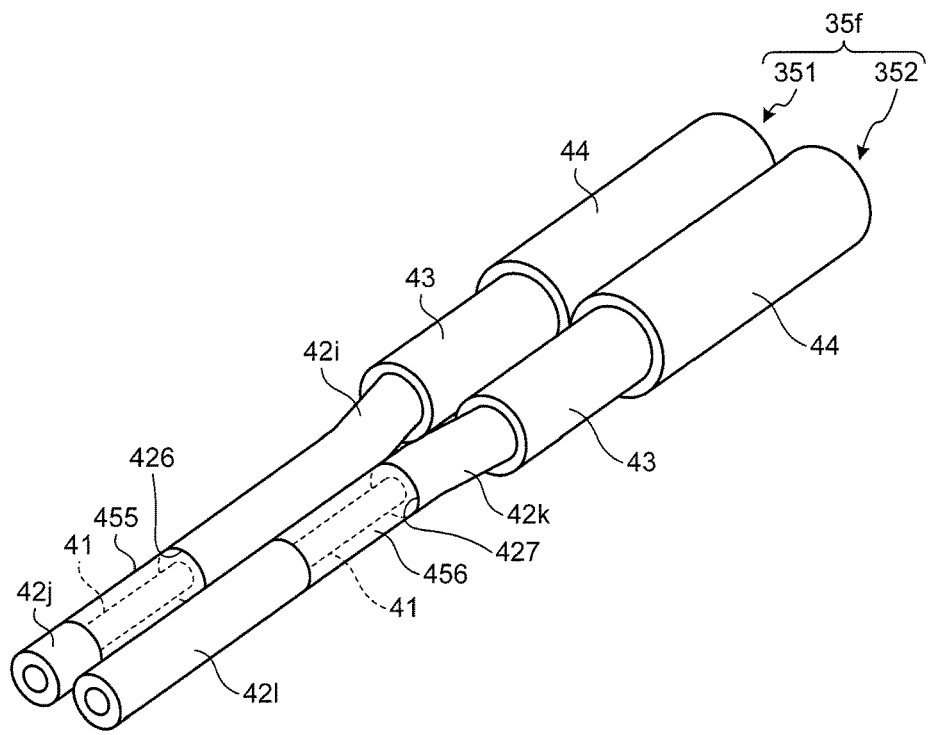
FIG. 15 is a perspective diagram illustrating a cable of a cable connection structure according to a second embodiment of the present invention.
Figure 16:
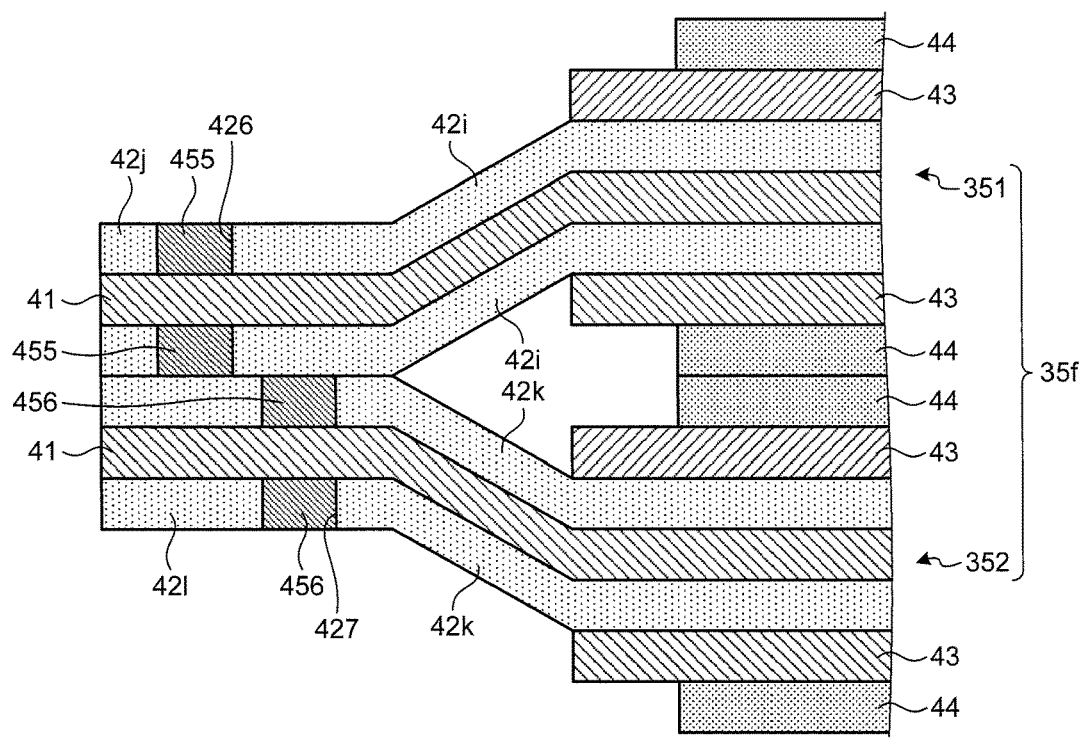
FIG. 16 is a cross section diagram illustrating the cable of the cable connection structure according to the second embodiment of the present invention.

Next, a second embodiment will be described. In the second embodiment, a case in which a plurality of coaxial cables are included will be described. To structural elements that are the same as those described above for FIG. 3 and the like, the same reference signs will be appended. FIG. 15 is a perspective diagram illustrating coaxial cables 351 and 352 (cable group 35f) of a cable connection structure according to this second embodiment. FIG. 16 is a cross section diagram illustrating the coaxial cables 351 and 352 (cable group 35f) of the cable connection structure according to the second embodiment.

The cable group 35f is formed of the plurality of coaxial cables 351 and 352 (two cables in this second embodiment) and contacts the circuit board with the two coaxial cables 351 and 352 put together.

The coaxial cable 351 includes: a core wire 41 formed of a conductive body; a first inner insulation layer 42i, which is formed of an insulator, covers an outer periphery of the core wire 41, and has at a distal end side thereof an exposing portion 426 that exposes the core wire 41; a second inner insulation layer 42j, which is provided at the distal end of the core wire 41 and covers a part of the exposing portion 426; a shield wire 43, which covers an outer periphery of the first inner insulation layer 42i and is formed of a conductive body; and an outer insulation layer 44, which covers at outer periphery of the shield wire 43 and is formed of an insulator. In the coaxial cable 351, at an end portion at a side connected to the circuit board 34, the first inner insulation layer 42i, the shield wire 43, and the outer insulation layer 44 are formed by being subjected to a step-stripping process.

The coaxial cable 351 includes, in the exposing portion 426 between the first inner insulation layer 42i and the second inner insulation layer 42j, a latching portion 455 (first latching portion), which is fixed to the core wire 41, is fitted into the exposing portion 426, and is latched onto the first inner insulation layer 42i and holds the core wire 41. The latching portion 455 is formed by being filled into, by a plating process, an inner space formed by the exposing portion 426. When that is done, a diameter of the latching portion 455 in a direction orthogonal to a direction, in which the coaxial cable 351 extends, is preferably equal to or less than a diameter of the first inner insulation layer 42i in the direction orthogonal to the direction, in which the coaxial cable 351 extends. Further, the latching portion 455 is formed of an electrically conductive material, such as nickel (Ni).

The coaxial cable 352 includes: a core wire 41 that is formed of a conductive body; a first inner insulation layer 42k, which is formed of an insulator, covers an outer periphery of the core wire 41, and has at a distal end side thereof an exposing portion 427 that exposes the core wire 41; a second inner insulation layer 42l, which is provided at a distal end of the core wire 41 and covers a part of the exposing portion 427; a shield wire 43, which covers an outer periphery of the first inner insulation layer 42k and is formed of a conductive body; an outer insulation layer 44, which covers an outer periphery of the shield wire 43 and is formed of an insulator. In the coaxial cable 352, at an end portion at a side connected to the circuit board 34, the first inner insulation layer 42k, the shield wire 43, and the outer insulation layer 44 are formed by being subjected to a step-stripping process.

The coaxial cable 352 includes, in the exposing portion 427 between the first inner insulation layer 42k and the second inner insulation layer 42l, a latching portion 456 (first latching portion), which is fixed to the core wire 41, is fitted into the exposing portion 427, and is latched onto the first inner insulation layer 42k and holds the core wire 41. The latching portion 456 is formed by being filled into, by a plating process, an inner space formed by the exposing portion 427. When that is done, a diameter of the latching portion 456 in a direction orthogonal to a direction, in which the coaxial cable 352 extends, is preferably equal to or less than a diameter of the first inner insulation layer 42k in the direction orthogonal to the direction, in which the coaxial cable 352 extends. Further, the latching portion 456 is formed of an electrically conductive material, such as nickel (Ni).

When the two coaxial cables 351 and 352 are adjacent to each other, the exposing portion 426 and the latching portion 455, as well as the exposing portion 427 and the latching portion 456, are provided at positions not adjacent to each other. Specifically, distances of a rear end of the exposing portion 426 and a distal end of the exposing portion 427 from distal ends of the coaxial cables 351 and 352 are different from each other. Accordingly, when the coaxial cables 351 and 352 are in contact with each other, the latching portion 455 and the latching portion 456 do not contact each other.

According to the above described second embodiment, because the plurality of coaxial cables 351 and 352 are fixed to the core wires 41 and the latching portions 455 and 456 latched onto the first inner insulation layers 42i and 42k are provided at the different positions, even if a load in a pulling direction acts on the core wires due to deformation of the cables or stripping at the other end after cable connection, or the like, connection between the end faces of the core wires and a connection bump can be prevented from being destroyed and reliability of connection between the cables and the circuit board can be improved.

Figure 17:
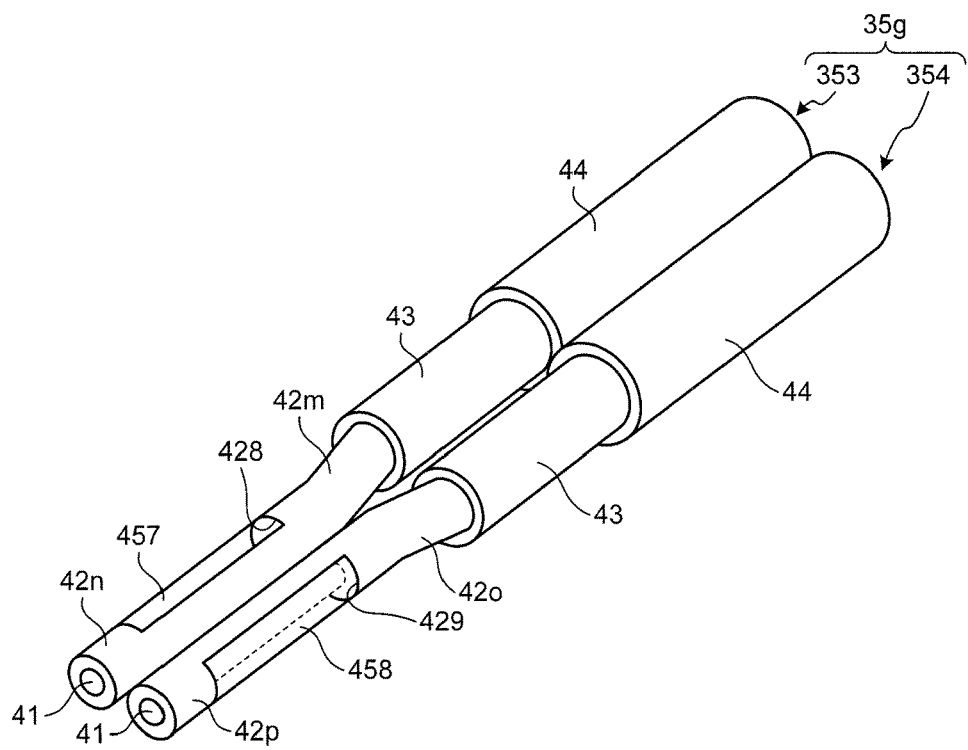
FIG. 17 is a perspective diagram illustrating a cable of a cable connection structure according to a modified example 2-1 of the second embodiment of the present invention.
Figure 18:
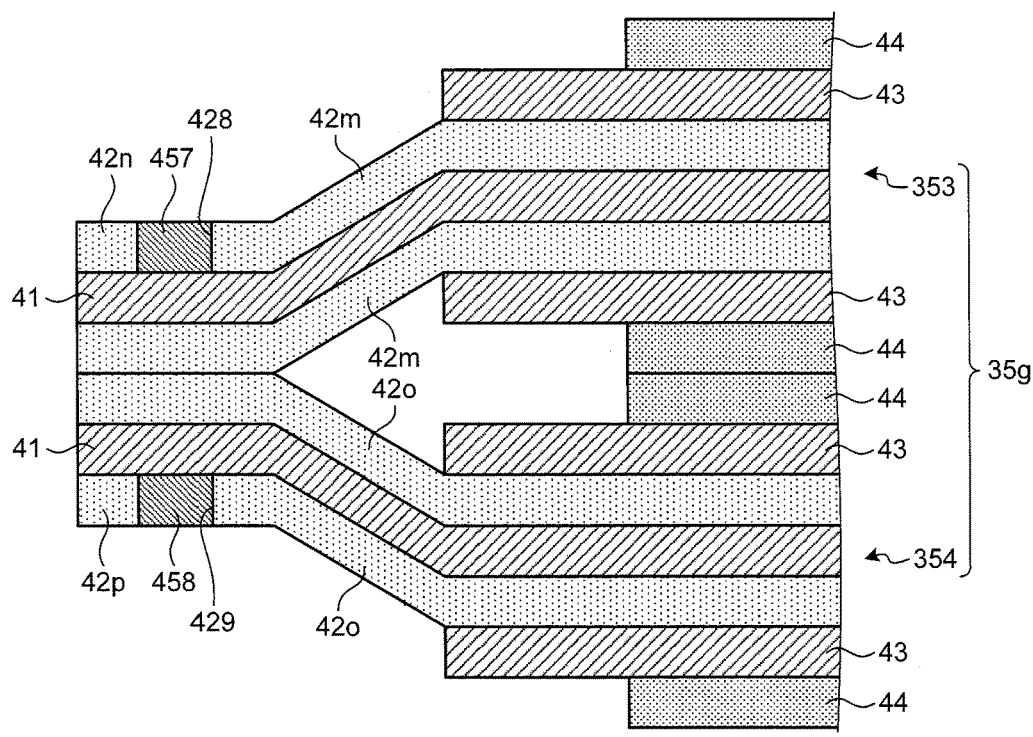
FIG. 18 is a cross section diagram illustrating the cable of the cable connection structure according to the modified example 2-1 of the second embodiment of the present invention.

FIG. 17 is a perspective diagram illustrating coaxial cables 353 and 354 (cable group 35g) of a cable connection structure according to a modified example 2-1 of this second embodiment. FIG. 18 is a cross section diagram illustrating the coaxial cables 353 and 354 (cable group 35g) of the cable connection structure according to the modified example 2-1 of the second embodiment. According to the above description of the second embodiment, the exposing portion and the latching portion are provided over a whole circumference of a cable side surface, but like in the modified example 2-1, an exposing portion and a latching portion may be provided partially on a peripheral surface.

The coaxial cable 353 includes: a core wire 41 formed of a conductive body; a first inner insulation layer 42m, which is formed of an insulator and covers an outer periphery of the core wire 41; a second inner insulation layer 42n, which covers an outer periphery of the core wire 41 and has, on a part of an outer surface thereof in a circumferential direction, an exposing portion 428 that exposes the core wire 41; a shield wire 43, which covers an outer periphery of the first inner insulation layer 42m and is formed of a conductive body; and an outer insulation layer 44, which covers an outer periphery of the shield wire 43 and is formed of an insulator. In the coaxial cable 353, at an end portion at a side connected to the circuit board 34, the first inner insulation layer 42m, the shield wire 43, and the outer insulation layer 44 are formed by being subjected to a step-stripping process.

The coaxial cable 353 includes, at the exposing portion 428 between the first inner insulation layer 42m and the second inner insulation layer 42n, a latching portion 457 (first latching portion), which is fixed to the core wire 41, is fitted into the exposing portion 428, and is latched onto the first inner insulation layer 42m and holds the core wire 41. The latching portion 457 is formed by being filled into, by a plating process, an inner space formed by the exposing portion 428. When that is done, a diameter of the latching portion 457 in a direction orthogonal to a direction, in which the coaxial cable 353 extends, is preferably equal to or less than a diameter of the first inner insulation layer 42m in the direction orthogonal to the direction, in which the coaxial cable 353 extends. Further, the latching portion 457 is formed of an electrically conductive material, such as nickel (Ni).

The coaxial cable 354 includes: a core wire 41 formed of a conductive body; a first inner insulation layer 42o, which is formed of an insulator and covers an outer periphery of the core wire 41; a second inner insulation layer 42p, which covers an outer periphery of the core wire 41 and has, in a part of an outer surface thereof in a circumferential direction, an exposing portion 429 that exposes the core wire 41; a shield wire 43, which covers an outer periphery of the first inner insulation layer 42o and is formed of a conductive body; and an outer insulation layer 44, which covers an outer periphery of the shield wire 43 and is formed of an insulator. In the coaxial cable 354, at an end portion at a side connected to the circuit board 34, the first inner insulation layer 42o, the shield wire 43, and the outer insulation layer 44 are formed by being subjected to a step-stripping process.

The coaxial cable 354 includes, in the exposing portion 429 between the first inner insulation layer 42o and the second inner insulation layer 42p, a latching portion 458 (first latching portion), which is fixed to the core wire 41, is fitted into the exposing portion 429, and is latched onto the first inner insulation layer 42o and holds the core wire 41. The latching portion 458 is formed by being filled into, by a plating process, an inner space formed by the exposing portion 429. When that is done, a diameter of the latching portion 458 in a direction orthogonal to a direction, in which the coaxial cable 354 extends, is preferably equal to or less than a diameter of the first inner insulation layer 42o in the direction orthogonal to the direction, in which the coaxial cable 354 extends. Further, the latching portion 458 is formed of an electrically conductive material, such as nickel (Ni).

The cable group 35g is formed by putting together the coaxial cables 353 and 354 such that surfaces of the second inner insulation layers 42n and 42p, the surfaces on which the exposing portions 428 and 429 are not arranged, contact each other. Thereby, even when the second inner insulation layers 42n and 42p are adjacent to each other and distances of the exposing portions 428 and 429 from axial cable distal ends are equal to each other, the latching portions 457 and 458 do not contact each other.

Accordingly, by arranging the hollowed portion and the latching portion partially in the circumferential direction, extension of the coaxial cables in a longitudinal direction due to formation of the hollowed portions at the different arrangement positions like in the above described second embodiment can be suppressed, and even if a load in a pulling direction acts on the core wires due to deformation of the cables, stripping at the other end after cable connection, or the like, connection between the end faces of the core wires 41 and a connection bump can be prevented from being destroyed and reliability of connection between the cables and the circuit board can be improved.

Third Embodiment

Figure 19:
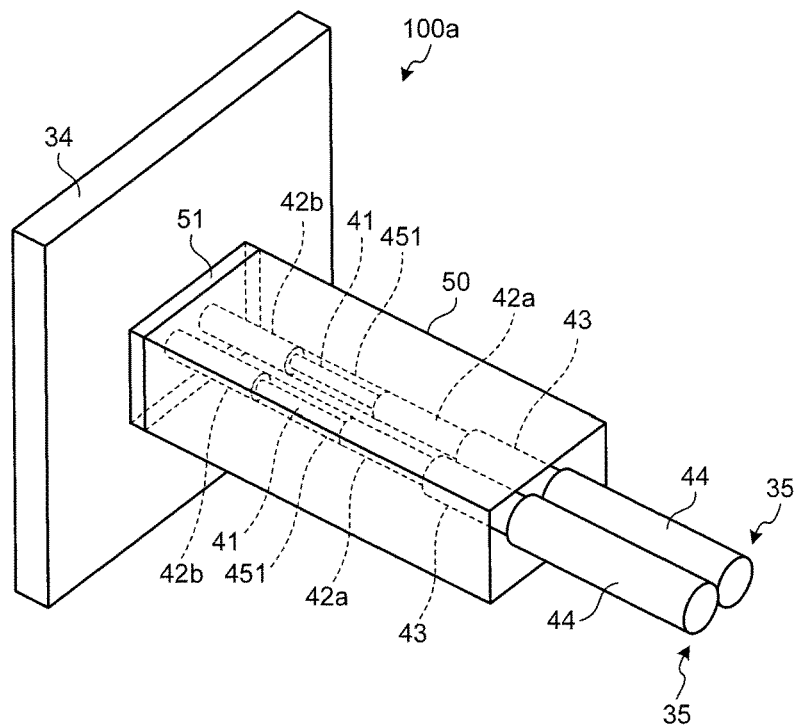
FIG. 19 is a perspective diagram illustrating a cable of a cable connection structure according to a third embodiment of the present invention.
Figure 20:
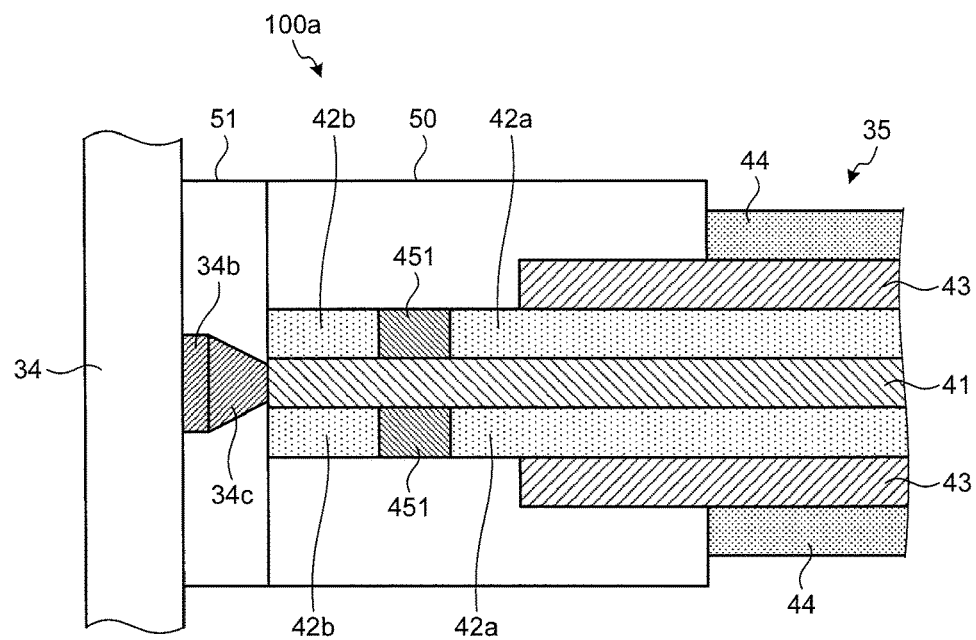
FIG. 20 is a cross section diagram illustrating the cable connection structure according to the third embodiment of the present invention.

Next, a third embodiment will be described. In the third embodiment, a case in which a plurality of the coaxial cables 35 are included will be described. To structural elements that are the same as those described above for FIG. 3 and the like, the same reference signs will be appended. FIG. 19 is a perspective diagram of a cable connection structure 100a according to the third embodiment. FIG. 20 is a cross section diagram illustrating the cable connection structure 100a according to the third embodiment.

The cable connection structure 100a illustrated in FIGS. 19 and 20 includes the circuit board 34 and a plurality of the coaxial cables 35, which are described above, and a holding member 50 that holds a part of the coaxial cables 35. The holding member 50 holds the coaxial cables 35 so that end faces of the coaxial cables 35 are aligned and holds the coaxial cables 35 correspondingly to arrangement positions of the electrodes 34b to which the respective coaxial cables 35 are connected.

Further, in the cable connection structure 100a, a reinforcement member 51 is provided, which is formed of an insulating material and covers the electrode 34b and the connection bump 34c, between the circuit board 34 and the holding member 50, in order to supplement connection strength of the connection bump 34c.

According to the above described third embodiment, by the plurality of coaxial cables 35 having the latching portion 451, which is fixed to the core wire 41 and is latched onto the first inner insulation layer 42a and providing the holding member 50, which holds the plurality of coaxial cables 35, even if a load in a pulling direction acts on the core wire by deformation of the cables, stripping at the other end after cable connection, or the like, connection between end faces of the core wires 41 the connection bumps can be more infallibly prevented from being destroyed and reliability of connection between the cables and the circuit board can be improved. Further, by fixing the positions of the plurality of coaxial cables 35 by the holding member 50, connection operations between the circuit board 34 and the plurality of coaxial cables 35 can be facilitated. Further, the holding member 50 and the latching portion 451 can be formed of a resin material, and in this case, the holding member 50 and the latching portion 451 may be integrally formed of the resin material.

Figure 21:
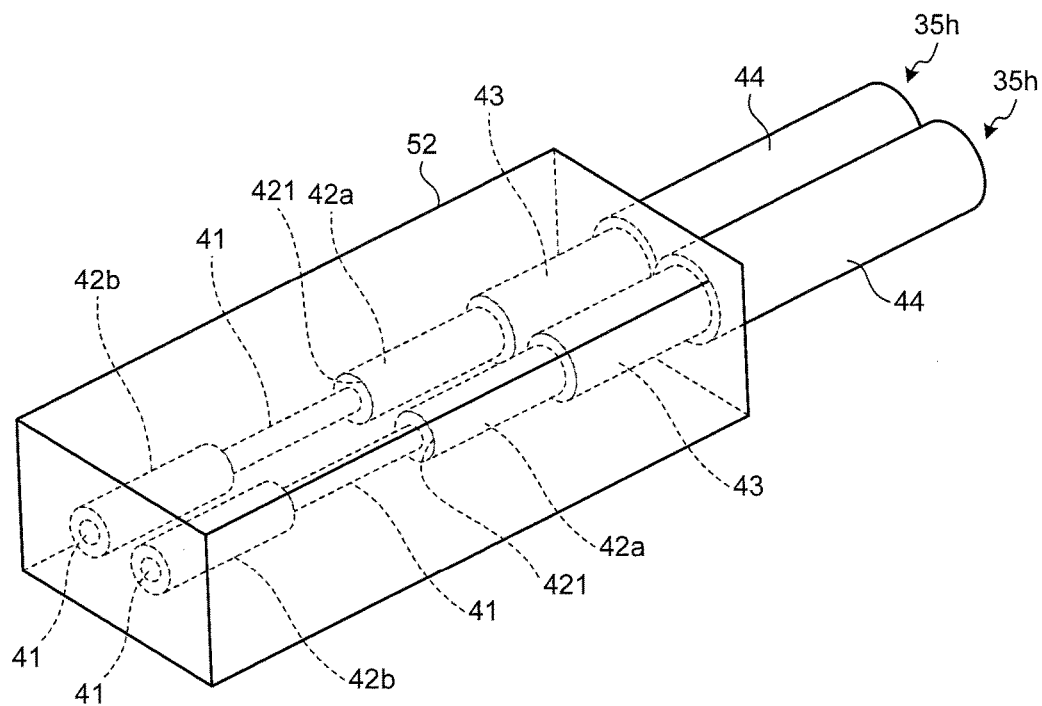
FIG. 21 is a perspective diagram illustrating a configuration of main parts of a cable connection structure according to a modified example 3-1 of the third embodiment of the present invention.
Figure 22:
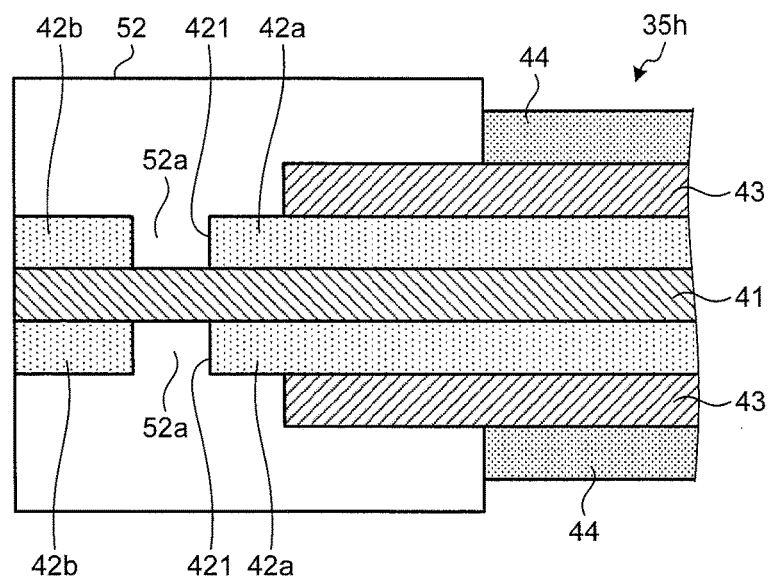
FIG. 22 is a cross section diagram illustrating the configuration of the main parts of the cable connection structure according to the modified example 3-1 of the third embodiment of the present invention.

FIG. 21 is a perspective diagram of a configuration of main parts of a cable connection structure according to a modified example 3-1 of the third embodiment. FIG. 22 is a cross section diagram of the configuration of the main parts of the cable connection structure according to the modified example 3-1 of the third embodiment.

As illustrated in FIGS. 21 and 22, the cable connection structure according to the modified example 3-1 includes: a plurality of coaxial cables 35h connected to the circuit board 34, instead of the coaxial cables 35; and a holding member 52 that holds a part of the coaxial cables 35h, instead of the holding member 50. The holding member 52 holds the coaxial cables 35h such that end faces of the coaxial cables 35h are aligned and holds the coaxial cables 35h correspondingly to arrangement positions of electrodes to which the respective coaxial cables 35h are connected.

Further, in the holding member 52, a latching portion 52a (first latching portion) is formed, which is latched onto the first inner insulation layer 42a and holds the core wire 41 by being provided protruded correspondingly to the exposing portion 421, having a protruded end surface fixed to the core wire 41, and being fitted into the exposing portion 421.

Like in the above described modified example 3-1, a configuration in which the holding member 52 has the latching portion 52a, which is fixed to the core wire 41 and latched onto the first inner insulation layer 42a is also applicable, and thereby, even if a load in a pulling direction acts on the core wires due to deformation of the cables, stripping at the other end after cable connection, or the like, connection between the end faces of the core wire 41 and shield wire 43 and the connection bumps can be prevented from being destroyed and reliability of connection between the cables and the circuit board can be improved.

Figure 23:
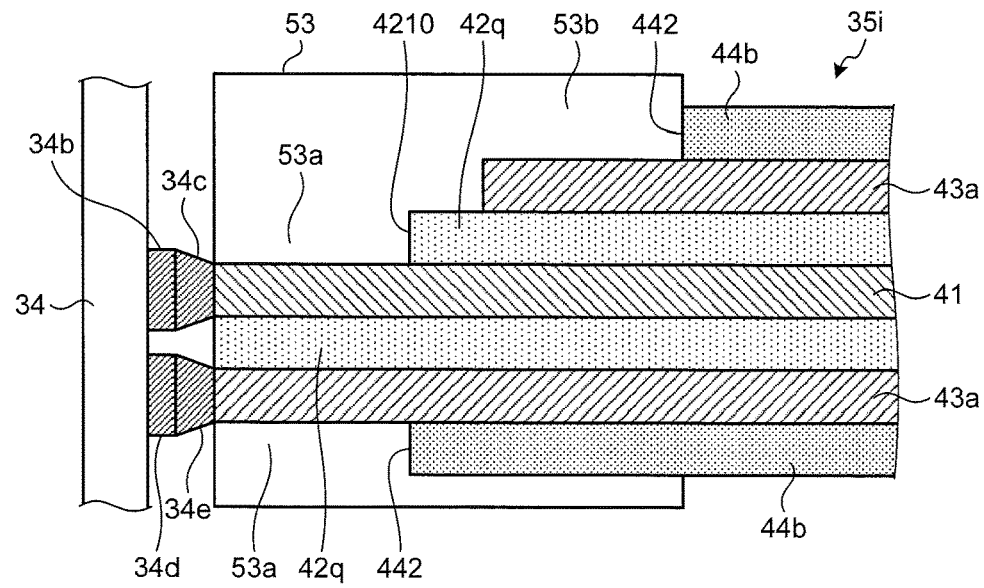
FIG. 23 is a cross section diagram illustrating a configuration of main parts of a cable connection structure according to a modified example 3-2 of the third embodiment of the present invention.
Figure 24:
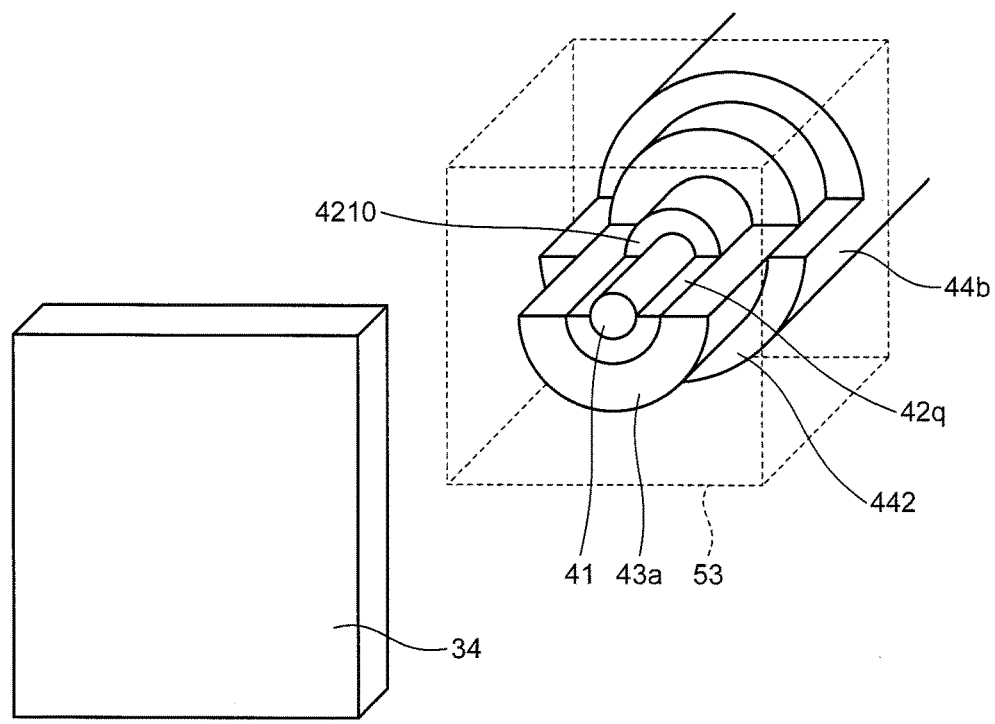
FIG. 24 is a perspective diagram illustrating a configuration of the main parts of the cable connection structure according to the modified example 3-2 of the third embodiment of the present invention.

FIG. 23 is a cross section diagram of a configuration of main parts of a cable connection structure according to a modified example 3-2 of the third embodiment. FIG. 24 is a perspective diagram of the configuration of the main parts of the cable connection structure according to the modified example 3-2 of the third embodiment. Like the modified example 3-2 illustrated in FIG. 23, without providing the second inner insulation layer 42b, instead of the holding member 52 of the above described modified example 3-1, a holding member 53 may be used, which has a latching portion (first and second latching portions) formed therein, which is latched onto the first inner insulation layer 42q and an outer insulation layer 44b and holds the core wire 41 and a shield wire 43a. Further, in FIG. 23, the shield wire 43a and an electrode 34d are fixed by a connection bump 34e and electrically connected to each other.

In the outer insulation layer 44b, a hollowed portion 442, which is hollowed at a distal end thereof, such that different lengths of the shield wire 43a are exposed. The shield wire 43a is formed such that at a distal end thereof, a part of a side surface thereof exposes the first inner insulation layer 42q. Further, in the first inner insulation layer 42q, at a portion exposed by the shield wire 43a, an exposing portion 4210 that exposes the core wire 41 is formed.

In the holding member 53, a latching portion 53a, which is fixed to the core wire 41 and the shield wire 43a, and is latched onto the first inner insulation layer 42q (exposing portion 4210) and a part of the outer insulation layer 44b (hollowed portion 442) and holds the core wire 41 and the shield wire 43a; and a latching portion 53b (second latching portion), which is fixed to the shield wire 43a, and is latched onto a part of the outer insulation layer 44b (hollowed portion 442) and holds the shield wire 43a, are formed. The latching portion 53a has both of functions of the first and second latching portions.

Like in the above described modified example 3-2, a configuration in which the holding member 53 has latching portions 53a and 53b, which are fixed to the core wire 41 and latched onto the first inner insulation layer 42q and the outer insulation layer 44b is also applicable, and thereby, even if a load in a pulling direction acts on the core wire due to deformation of the cable, stripping at the other end after cable connection, or the like, connection between end faces of the core wire 41 and shield wire 43a and the connection bumps can be prevented from being destroyed and reliability of connection between the cable and the circuit board can be improved.

In the present specification, "to hollow" includes exposing a part of an outer periphery of the core wire 41 like in the coaxial cable 35i illustrated in FIG. 23.

According to the above described embodiments, the latching portions are formed of an electrically conductive material, but latching portions made of an insulating material, such as a resin, are also applicable and in that case, the latching portions may contact each other upon contact of the coaxial cables and the shield wire may cover an outer periphery of the latching portion. Further, in that case, the shield wire may also cover outer peripheries of the second inner insulation layer and the third inner insulation layer.

Further, in the first to third embodiments, the coaxial cables have been described as examples, but of course, application to a non-coaxial cable or the like made only of a core wire of a shield wire is also possible.

Further, in the first to third embodiments, the imaging unit that is mounted on the distal end portion of the insertion tool of the endoscope apparatus is described as an example, but of course, application to electronic imaging modules of various modes is possible, such as digital cameras and digital video cameras, in addition to portable telephones having imaging functions.

According to some embodiments, a latching portion, which is fixed to a core wire and is latched onto an inner insulation layer, is provided, and the inner insulation layer is latched onto the core wire. With this structure, even if a load in a pulling direction acts on the core wire due to deformation of a cable, stripping at the other end after cable connection, or the like, connection between an end face of the core wire and a connection bump can be prevented from being destroyed and reliability of connection between the cable and a circuit board can be improved.

As described above, a cable, a cable connection structure for connecting the cable to a substrate, and an imaging apparatus according to the invention are useful for improving reliability of the connection between the cable and the circuit board.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection structure, comprising:
a first cable that has at least a first core wire that is electrically conductive and a first inner insulation layer that covers an outer periphery of the first core wire and has a first exposing portion that exposes the first core wire at a distal end side of the first inner insulation layer;
a first latching portion that is fixed to the first core wire in the first exposing portion, and is latched onto the first inner insulation layer and holds the first core wire by coming into contact with the first inner insulation layer;
a second cable that has at least a second core wire that is electrically conductive and a second inner insulation layer that covers an outer periphery of the second core wire and has a second exposing portion that exposes the second core wire at a distal end side of the second inner insulation layer;
a second latching portion that is fixed to the second core wire in the second exposing portion, and is latched onto the second inner insulation layer and holds the second core wire by coming into contact with the second inner insulation layer;

a circuit board that has an electrode electrically connected to each of the first core wire and the second core wire; and a holding member that holds the first cable and the second cable, wherein the first latching portion and the second latching portion are integrally formed in the holding member.

2. The cable connection structure according to claim 1, wherein when the first cable and the second cable are adjacent to one another, the first exposing portion and the first latching portion of the first cable, and the second exposing portion and the second latching portion of the second cable are provided at positions not adjacent to one another.

3. The cable connection structure according to claim 1, wherein when the first cable and the second cable are adjacent to one another, the first and second exposing portions and the first and second latching portions are provided at a part of a non-contacting area between the first cable and the second cable on a peripheral surface of each of the first and second cables.

4. An imaging apparatus, comprising:

the cable connection structure according to claim 1; and an imaging element that is connected to an external electrode formed on the circuit board of the cable connection structure and converts light incident from outside into an electric signal.

\* \* \* \* \*